(12) United States Patent
Greenwood et al.

(10) Patent No.: US 7,186,837 B2
(45) Date of Patent: Mar. 6, 2007

(54) PREPARATION OF CABERGOLINE

(75) Inventors: Alan Greenwood, Hitchin (GB); Derek McHattie, Stotfold (GB); Parveen Bhatarah, Craniford (GB); Mark Philip Gamble, Hitchin (GB)

(73) Assignee: Resolution Chemicals, Stevenage (GB)

( * ) Notice: Subject to any disclaimer, the term of this patent is extended or adjusted under 35 U.S.C. 154(b) by 0 days.

(21) Appl. No.: 11/060,991

(22) Filed: Feb. 18, 2005

(65) Prior Publication Data
US 2005/0245560 A1 Nov. 3, 2005

(30) Foreign Application Priority Data
Apr. 30, 2004 (GB) .................................. 0409785.3

(51) Int. Cl.
*C07D 457/04* (2006.01)
*C07D 457/00* (2006.01)
(52) U.S. Cl. .......................................... 546/69; 546/67
(58) Field of Classification Search .................. 546/69, 546/67
See application file for complete search history.

(56) References Cited

U.S. PATENT DOCUMENTS

| | | | |
|---|---|---|---|
| 3,920,664 A | 11/1975 | Clemens et al. | |
| 4,180,582 A | 12/1979 | Kornfeld et al. | |
| 4,202,979 A | 5/1980 | Kornfeld et al. | |
| 4,229,451 A | 10/1980 | Fehr et al. | |
| 4,246,265 A | 1/1981 | Kornfeld et al. | |
| 4,526,892 A | 7/1985 | Salvati et al. | |
| 4,675,404 A | 6/1987 | Bernardi et al. | |
| 4,782,152 A | 11/1988 | Misner | |
| 5,382,669 A | 1/1995 | Candiani et al. | |
| 6,395,901 B1 | 5/2002 | Mangia et al. | |

FOREIGN PATENT DOCUMENTS

| | | |
|---|---|---|
| CH | 535235 | 3/1973 |
| CH | 535236 | 3/1973 |
| CZ | 144634 | 7/1972 |
| CZ | 287176 | 4/1999 |
| FR | 2479829 | 10/1981 |
| GB | 1451724 | 10/1976 |
| GB | 1499420 | 2/1978 |
| GB | 2014140 A | 8/1979 |
| GB | 2103603 A | 2/1983 |
| GB | 0409785-3 | 6/2004 |
| WO | WO 01/70740 A1 | 9/2001 |
| WO | WO 01/72746 A1 | 10/2001 |
| WO | WO 01/72747 A1 | 10/2001 |
| WO | WO 03/78392 A2 | 9/2003 |
| WO | WO 03/78433 A1 | 9/2003 |
| WO | WO 04/101510 A2 | 11/2004 |

OTHER PUBLICATIONS

I. Candiani, W. Cabri, F. Zarini, A. Bedeschi and S. Penco, Synlett, The Ligand Effect in Copper (I)—Catalyzed Chemoselective Amide . . . , (1995), 605-606.

Sabatino, Sanseverino and Tonani, X-Ray Crystal Structure and Conformation Analysis of [Cabergoline] . . . , Il Farmaco, 50(3), (1995), 175-178.

E. Brambilla, E. di Salle, G. Briatico, S. Mantegani and A. Temperilli, Synthesis and Nidation Inhibitory Activity . . . , New Eur. J. Med. Chem., 24, (1989), 421-426.

S. Montegani, E. Brambilla and A. Ermoli, Synthesis of Tritium and Carbon-14 labeled N . . . , J. Labelled Compd. Radiopharm., vol. 29, No. 5., 519-533, (1991).

S. Ohno, Y. Adachi, M. Koumori, K. Mizukoshi, M. Nagasaka, K. Ichihara and El Kato, Synthesis and Structure . . . , Chem. Pharm. Bull., 42(7), vol. 42, No. 7, (1994), 1463-1473.

R. Battaglia, M. Strolin Benedetti, S. Mantegani, M.G. Castelli, G. Castelli, G. Cocchiara and P. Dostert, Disposition . . . , Xenobiotica, vol. 23, No. 12, (1993), 1377-1389.

J. Benes, A. Cerny, V. Miller and S. Kudrnac, Epimerization of Esters of Stereoisomeric . . . , Coll. Czech. Chem. Commun., vol. 48, (1983), 1333-1340.

A. Stoll and A. Hofman, Die Dihydroderivate der rechtsdrehenden . . . , Helv. Chim. Acta, vol. 29, Fasc. 3, (1946), 635-653.

P.S. Stadler, Eine einfache Veresterungsmethode im Eintopf-Verfahren, Helv. Chim. Acta, vol. 61, Fasc. 5, (1978), 1675-1681.

T. Fehr, P. Stadler and A. Hofman, Demethylierung des Lysergsauregerustes, Helv. Chim. Acta, vol. 53, Fasc. 8, (1970), 2197-2201.

J. Krepelka, A. Cerny, R. Kotva and M. Semonsky, Some 6-Alkyl Derivatives of D-8-Cyanomethyl . . . , Coll. Czech. Chem. Commun., vol. 42, (1977), 1209-1215.

W.A. Jacobs and L.C. Craig, Isomeric Dihydrolysergic Acids and the Structure of Lysergic Acid, J. Biol. Chem., (1936), 227-239.

A. Cerney and M. Semonsky, Mutterkornalkaloide, Pharmazie, vol. 26(12), (1971), 740-741.

E.C. Kornfeld, E. J. Fornefeld, G. B. Kline, M. J. Mann, R. G. Jones and R. B. Woodward, The Total Synthesis of Lysergic Acid, J. Am. Chem. Soc., (1956), 3087-3114.

C.Z. Zhang, J.H. Yang, and J. Zhou, Zhongguo Yi Xue Ke Xue Yuan Xue Bao, vol. 6, No. 1, (1984), 70-72.

A. Kleeman, J. Engel, B. Kutscher, D. Reichert, Georg Thieme Verlag, Pharmaceutical Substances, 4th ed., 312-313, 2001.

C. Dollery and Churchill Livingstone, Therapeutic Drugs, 2nd ed., (1999), C1-C4.

K. Parfitt, The Pharmaceutical Press, Martindale, 32nd ed., (1999), 1135-1136.

(Continued)

*Primary Examiner*—Charanjit S. Aulakh
(74) *Attorney, Agent, or Firm*—Rakoczy Molino Mazzochi Siwik LLP

(57) ABSTRACT

The present invention discloses a method for preparing cabergoline form I by combining cabergoline and a solvent comprising ethylbenzene to form a solvate and obtaining form I from the solvate. Also disclosed in a method for preparing cabergoline form I by combining cabergoline and a first solvent to form a solution and additionally including a second solvent to the solution, followed by crystallization to form cabergoline form I. Further disclosed is a solvate form of cabergoline comprising cabergoline and ethylbenzene and, optionally, n-heptane.

28 Claims, No Drawings

OTHER PUBLICATIONS

M.D. Gottwald, J.L. Bainbridge, G.A. Dowling, M.J. Aminoff and B.K. Alldredge, Ann. Pharmacother., vol. 31, (1997), 1205-1217.

L.R. Wiseman and F. Fitton, Cabergoline—A Review of its Efficacy in the Treatment of Parkinson's Disease, CNS Drugs, vol. 12(6) (1999), 485-497.

K. Ichikawa and M. Kojima, Nippon Yakurigaku Zasshi, vol. 117, (2001), 395-400.

The Merck Index, 13th ed., (2001), 270.

V. Gotor, Non-Conventional Hydrolase Chemistry: Amide and Carbamate Bond Formation Catalyzed by Lipases, Bioorg. Med. Chem., vol. 7, (1999), 2189-2197.

A.M. Crider, R. Grubb, K.A. Bachmann and A.K. Rawat, Convenient Synthesis of 6-nor-9,10-dihydrolysergic Acid Methyl Ester, J. Pharm. Sci., vol. 70, No. 12, (1981), 1319-1321.

R.A. Olofson and J. Martz, A New Reagent for the Selective, High Yield N-Dealkylation of Tertiary Amines . . . , J. Org. Chem., vol. 49, (1984), 2081-2082.

R.A. Olofson and D.E. Abbott, Tests of a Piperidino Mask for the Protection of Functionalized Carbon Sites in Multistep Syntheses, J. Org. Chem., vol. 49, (1984), 2795-2799.

C. Allievi and P. Dostert, Quantitative Determination of Cabergoline in Human Plasma . . . , Rapid Commun. Mass Spectrom., vol. 12, (1998), 33-39.

V. Prelog, B.C. McKusick, J.R. Merchant, S. Julia and M. Wilhelm, Helv. Chim. Acta., vol. 39, (1956), 498-504.

J.R. Vaughan, Acylalkylcarbonates as Acylating Agents for the Synthesis of Peptides, J. Am. Chem. Soc., vol. 73, (1951), 3547.

E.R.H. Walker, The Functional Group Selectivity of Complex Hydride Reducing Agents, Chem. Soc. Rev., vol. 5, (1976), 23-51.

M.J. Kornet, P.A. Thio amd S.I. Tan, The Borane Reduction of Amido Esters, J. Org. Chem., vol. 33, No. 9, (1968), 3637-3639.

J.M. Lalancette, A. Freche, J.R. Brindle and M. Laliberte, Reductions of Functional Groups with Sulfurated Borohydrides. Synthesis, (1972), 526-532.

G. Cainelli, L. Caglioti and W. Barberi, Farmaco, Ed. Sci., vol. 22, No. 6, (1967), 456-462.

R.C. Larock, Comprehensive Organic Transflormations, 2nd ed., Wiley VCH, (1999), 1940-1977.

J.M. Humphrey and A.R. Chamberlin, Chemical Synthesis of Natural Product Peptides . . . , Chem. Rev., vol. 97, (1997), 2243-2266.

L.A. Carpino, A. Elfaham and F. Albericio, Racemization Studies During Solid-Phase Peptide Synthesis . . . , Tetrahedron Letters, vol. 35 (1994), 2279-2282.

J.C. Spetzler, M. Meldal, J. Felding, P. Vedso and M. Begtrup, Novel Acylation Catalysts in Peptide Synthesis . . . , J. Chem. Soc., Perkin Trans. vol. 1, (1998), 1727-1731.

F.S. Gibson, M.S. Park and H. Rapoport, Bis[[4-(2,2-dimethyl-1,3-dioxolyl)]methyl]-carbodiimide (BDDC) . . . , J. Org. Chem., vol. 59, (1994), 7503-7507.

F.S. Gibson and H. Rapoport, Carboxy Terminus Coupling Using 1,1'-Carbonylbis (3-methylimidazolium triflate) (CBMIT) . . . , J. Org. Chem., vol. 60, (1995), 2615-2617.

M. Soledad de Castro and J.V. Sinisterra-Gago, Lipase-Catalyzed Synthesis of Chiral Amides . . . , Tetrahedron, vol. 54, (1998), 2877-2892.

V.M. Sanchez, F. Rebolledo and V. Gotor, Candida Antarctica Lipase-Catalyzed Doubly Enantioselective Aminolysis Reactions . . . , J. Org. Chem., vol. 64, (1999), 1464-1470.

V.M. Stepanov, Proteinases as Catalysts in Peptide Synthesis, Pure and Appl. Chem., vol. 68, No. 6, (1996), 1335-1339.

G. Marzoni, W. Garbrecht, P. Fludzinski, and M. Cohen, 6-Methylergoline-8-carboxylic Acid Esters . . . , J. Med. Chem., vol. 30, (1987) 1823-1826.

US 7,186,837 B2

PREPARATION OF CABERGOLINE

This application claims priority to United Kingdom Patent Application No. GB 0409785-3, filed on Apr. 30, 2004. This application is hereby incorporated by reference in its entirety.

FIELD OF THE INVENTION

The present application relates to preparation of cabergoline, in particular a new solvate form of cabergoline and its use in preparation of cabergoline form I.

BACKGROUND OF THE INVENTION

Cabergoline is an ergoline derivative with formula 1 ((6-allylergolin-8β-yl)-carbonyl)-1-(3-dimethylaminopropyl)-3-ethylurea. It is known for treatment of a number of diseases, including CNS disorders, reversible obstructive airways disease, prolactin inhibition, for controlling intraocular pressure and for treating glucoma.

A number of different forms of cabergoline are known and, by way of example, PCT patent publication no. WO 01/72747 describes form II and PCT patent publication no. WO 01/72746 describes form VII.

Preparation of cabergoline Form I is described in PCT patent publication nos. WO 01/70740, WO 03/078392 and WO 03/078433. It is known from PCT patent publication no. WO 01/70740 to prepare crystalline cabergoline form I from a solvent comprising a toluene/diethylether mixture. From PCT patent publication nos. WO 03/078392 and WO 03/078433, it is known to prepare a solvate of cabergoline and toluene, and obtain crystalline form I by drying the solvate.

It is desired, however, to prepare crystalline cabergoline of form I having high purity.

It is also desired to prepare cabergoline form I having a particle size (following crystallization) that is relatively small and which requires no or relatively little milling to obtain the particle size desired in the eventual pharmaceutical product. Milling and other such processing is undesirable as it tends to lead to conversion of pure polymorphic forms of cabergoline into polymorphic mixtures. One problem with the methods described in PCT patent publication no. WO 03/078433 and other references is that crystals of cabergoline form I are formed having a relatively large particle size.

It is also desired to provide a process for preparation of cabergoline in which conversion of the intermediate solvate to the final cabergoline form I is quick and efficient. A difficulty with known processes (e.g., those described in within PCT patent publication no. WO 03/078433) for this conversion is that protracted drying periods (i.e., in excess of 48 hours) are required to remove the solvent from the solvate.

SUMMARY OF THE INVENTION

The present invention discloses a method for preparing cabergoline form I by combining cabergoline and a solvent comprising ethylbenzene to form a solvate and obtaining form I from the solvate. Also disclosed in a method for preparing cabergoline form I by combining cabergoline and a first solvent to form a solution and additionally including a second solvent to the solution, followed by crystallization to form cabergoline form I. Further disclosed is a solvate form of cabergoline comprising cabergoline and ethylbenzene and, optionally, n-heptane.

DETAILED DESCRIPTION OF THE INVENTION

Accordingly, the present invention provides a method of preparation of form I of cabergoline in which cabergoline is dissolved in a solvent (e.g., ethylbenzene) to form a solution (e.g., a gel). A second solvent is optionally added to form Cabergoline form I.

In one preferred method of the invention, cabergoline form I is obtained by forming a solvate of cabergoline and ethylbenzene, optionally further comprising n-heptane, and obtaining cabergoline form I from this solvate.

A further method of the invention comprises dissolving cabergoline in a solvent comprising ethylbenzene to form a solvate and drying the solvate to obtain cabergoline form I.

In a method of the invention set out in more detail in the examples, cabergoline is dissolved in a solvent which comprises ethylbenzene and the solution cooled to a temperature of −5° C. or below. The solvent preferably comprises at least 75% by volume ethylbenzene, and is ethylbenzene in a specific embodiment.

Also provided by the present invention is cabergoline form I obtained by a method of the invention and a solvate form of cabergoline comprising cabergoline, a solvent such as ethylbenzene and, optionally, a second solvent such as n-heptane.

In one embodiment of the invention, cabergoline is dissolved in ethylbenzene. This is conveniently done at room temperature, typically about 25–30° C. and the resulting solution is preferably filtered to remove particulate material. The temperature of the solution is then lowered to about −5° C. or below, preferably −10° C. or below and a precipitate of cabergoline formed. This can be encouraged by stirring and also by seeding, for example using crystalline cabergoline form I. Next, an anti-solvent (i.e., a solvent in which the cabergoline-ethylbenzene solvate is highly insoluble) is added. It is preferable that the anti-solvent comprises hexane, heptane, diethylether, isopropylether, tetrabutylmethylether or mixtures of these solvents. More preferably, the anti-solvent comprises heptane. Most preferably, the anti-solvent comprises n-heptane.

The addition of the anti-solvent results in formation and precipitation of a cabergoline-ethylbenzene solvate, forming a slurry which can be filtered to recover the solvate, optionally washed, for example with further anti-solvent, and then dried to yield form I cabergoline in high purity.

It is also contemplated in accordance with the present invention that the addition of the anti-solvent results in a solution, which can then be crystallized by drying via various routes to yield cabergoline form I.

The ratio of the first, ethylbenzene-containing solvent to the second, anti-solvent, is generally in the range 4–10:5–20 volumes, preferably 5–7:8–15, more preferably 5–7:10–12 volumes. Particularly good results have been obtained with a solvent ratio of approximately 5–6:11.

The method has been found, advantageously, to yield cabergoline form I having a relatively small particle size, typically with a volume mean diameter (VMD) of less than 80 microns (μm), preferably less than 70 μm. In particular examples, described in more detail below, cabergoline form I has been obtained with a VMD of about 50 μm. Any milling of the product after crystallisation tends to result in loss of polymorph purity, and therefore this relatively small particle size is a significant advantage in preparation of a pharmaceutical product having cabergoline form I of small particle size in high purity.

A separate advantage of the method of the invention is that once wet solvate has been recovered by filtration this can rapidly be dried to form crystals of cabergoline form I, and can be dried more rapidly than possible hitherto.

Drying can be achieved in a number of different ways. For example, drying has been carried out under reduced pressure, at pressures of 900 mbar or less, 800 mbar or less and 700 mbar or less. In all cases, a dried, pure form I was obtained within 30 hours. It is also contemplated that drying can be carried out at elevated temperatures, for example at 50° C. or higher, preferably 60° C. or higher. Another option is for drying to be carried out in an inert gas atmosphere, typically containing nitrogen and/or argon or other inert gas at a concentration of 80% or higher by volume. Nitrogen or other inert gas blanket can be used or drying can be carried out in a stream of such an inert gas. It has been found that drying using an inert gas can be completed in less than 20 hours, representing a significantly reduced time compared to that required in the art. This is especially an advantage when preparing form I cabergoline at large scale.

The following examples illustrate the invention without intending to limit the scope of the invention.

EXAMPLES

Example 1

Preparation of Cabergoline Form I

Cabergoline (2 g, purity 99.9% by HPLC percentage peak area) was dissolved in 10 volumes of ethylbenzene at 25–30° C. The solution was polish filtered through a 0.1 μm filter and the filtrate was placed in the freezer at −23 to −17° C. on stirring. After 30 minutes the solution was seeded with pure cabergoline Form I. Stirring of the solution at −23 to −17° C. continued for a further 16 hours.

After this period, a pre-filtered solution of n-heptane (22 volumes), also at −23 to −17° C., was added dropwise to the ethylbenzene slurry over a 10-minute period.

Once the addition of n-heptane was complete, the slurry was stirred at −23 to −17° C. for a further 3.5 hours. The solid was then collected by filtration and washed with 2 volumes of cold n-heptane. A sample of the ethylbenzene/n-heptane solvate gave a DSC trace, which showed the presence of two peaks at 52.8 and 71.9° C.

The solid was then dried under a blanket of nitrogen for a period of 15 hours. After this period the DSC showed the presence of 1 peak at 101.5° C. The solid obtained was pure cabergoline Form I. The weight recovery was 86% and the purity by HPLC percentage peak area was 99.9%.

Example 2

Drying of Cabergoline

Example 2 repeats the method set forth in example 1, utilizing seven different drying steps. The various types of drying, together with the time to complete the same, are set forth in Table I, below.

TABLE I

| Example No. | Type of Drying | Time to Completion of Drying |
| --- | --- | --- |
| 2a | Vacuum at 900 mbar, at 20–25° C. | 29 hrs 15 min |
| 2b | Vacuum at 800 mbar, at 20–25° C. | 29 hrs 15 min |

TABLE I-continued

| Example No. | Type of Drying | Time to Completion of Drying |
| --- | --- | --- |
| 2c | Vacuum at 700 mbar, at 20–25° C. | 29 hrs 15 min |
| 2d | Blanket of $N_2$ (nitrogen) | 14 hrs 45 min |
| 2e | 60° C. at atmospheric pressure | 20 hrs 30 min |
| 2f | 40° C. at atmospheric pressure under a stream of $N_2$ (nitrogen) | 2 hrs |
| 2g | 40° C. at 87–111 mbar | 16–17 hr |

All experiments produced Cabergoline form I as confirmed by DSC and DRIFT spectroscopy.

Example 3

Particle Size Analysis

Example 3 repeated the method set forth in example 1 and measured the particle size of the resulting cabergoline form I. This particle size data was compared to 1) the particle size of cabergoline form I obtained according to WO 03/078433 (i.e., preparation of cabergoline form I from toluene and heptane) and 2) to the particle size of commercially available form II. The results are shown in Table II below.

TABLE II

| Polymorph | Solvent/Anti-solvent | $X_{10}$ (μm) | $X_{50}$ (μm) | $X_{90}$ (μm) | VMD (μm) |
| --- | --- | --- | --- | --- | --- |
| Cabergoline Form I | (Ethylbenzene/heptane) | 14.60 | 39.74 | 103.47 | 49.59 |
| Cabergoline Form I (from WO 03/74833) | (Toluene/heptane) | 36.67 | 100.05 | 149.69 | 96.01 |
| Cabergoline Form II | | 46.68 | 117.56 | 159.36 | 111.26 |

$X_{10}$, as used in Table II, is defined as the particle size at which the cumulative percentage undersize is 10 (i.e., the bottom 10% of particles are less than or equal to the stated size). $X_{50}$ means the median particle size and $X_{90}$ is defined as the particle size at which the cumulative percentage undersize is 90 (i.e., the bottom 90% of particles are less than or equal to the stated size).

The use of the terms "a" and "an" and "the" and similar references in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

We claim:

1. A method of preparing of cabergoline form I, comprising forming a solvate including cabergoline and ethylbenzene, and obtaining form I from the solvate.

2. The method of claim 1, wherein the cabergoline form I is obtained from the solvate by drying.

3. The method of claim 2, wherein the drying is performed at a pressure of 900 mbar or less.

4. The method of claim 2, wherein the drying occurs at a temperature of 50° C. or higher.

5. The method of claim 2, wherein the drying occurs in an inert gas atmosphere.

6. The method of claim 5, wherein the inert gas is selected from the group consisting of nitrogen or argon gas.

7. The method of claim 5, wherein the inert gas atmosphere comprises a gas mixture including 80% inert gas.

8. The method of claim 5, wherein the inert gas atmosphere comprises 5% or less oxygen.

9. A method according to claim 1, wherein the solvate is formed by dissolving cabergoline in a solvent.

10. The method of claim 9, wherein the solvent comprises ethylbenzene.

11. The method of claim 9, wherein the solvent comprises at least 75% by volume ethylbenzene.

12. The method of claim 10, wherein the solvate is cooled to a temperature of −5° C. or below.

13. A method of preparing cabergoline form I, comprising dissolving cabergoline in a first solvent comprising ethylbenzene to form a solution, and obtaining form I from the solution.

14. The method of claim 13, further comprising adding a second solvent to the solution.

15. The method of claim 14, wherein the second solvent is selected from the group consisting of hexane, heptane, diethylether, isopropylether, tetrabutylmethylether, and mixtures thereof.

16. The method of claim 14, wherein the second solvent is heptane.

17. The method of claim 14, wherein the second solvent is n-heptane.

18. The method of claim 14, further comprising the step of drying the solution to obtain cabergoline form I.

19. The method of claim 18, wherein the step of drying is performed at a pressure of 900 mbar or less.

20. The method of claim 18, wherein the step of drying occurs at a temperature of 50° C. or higher.

21. The method of claim 18, wherein the step of drying occurs in an inert gas atmosphere.

22. The method of claim 21, wherein the inert gas is selected from the group consisting of nitrogen and argon.

23. The method of claim 21, wherein the inert gas atmosphere comprises a gas mixture including 80% inert gas.

24. The method of claim 21, wherein the inert gas atmosphere comprises 5% or less oxygen.

25. A method of preparing cabergoline form I, comprising
   a) dissolving cabergoline in a first solvent to form a solution; and
   b) adding an anti-solvent to the solution to obtain cabergoline form I.

26. A method of preparing cabergoline form I, comprising
   a) dissolving cabergoline in a first solvent comprising ethylbenzene to form a solution; and
   b) adding a second solvent comprising n-heptane to the solution to obtain cabergoline form I.

27. A solvate form of cabergoline, comprising cabergoline and ethylbenzene.

28. The solvate form of claim 27, further comprising n-heptane.

* * * * *

UNITED STATES PATENT AND TRADEMARK OFFICE
CERTIFICATE OF CORRECTION

PATENT NO. : 7,186,837 B2 Page 1 of 1
APPLICATION NO. : 11/060991
DATED : March 6, 2007
INVENTOR(S) : Alan Greenwood et al.

It is certified that error appears in the above-identified patent and that said Letters Patent is hereby corrected as shown below:

On the title page of the Patent:

Item (73) Assignee: should read, Resolution Chemicals, Ltd., Stevenage (GB)

Signed and Sealed this

Sixth Day of November, 2007

JON W. DUDAS
*Director of the United States Patent and Trademark Office*